(12) United States Patent
McDonell (10) Patent No.: US 9,101,442 B2
(45) Date of Patent: Aug. 11, 2015

(54) REDUCED FRICTION VITRECTOMY PROBE

(75) Inventor: Brian William McDonell, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 107 days.

(21) Appl. No.: 13/304,792

(22) Filed: Nov. 28, 2011

(65) Prior Publication Data
US 2012/0158006 A1    Jun. 21, 2012

Related U.S. Application Data

(60) Provisional application No. 61/423,151, filed on Dec. 15, 2010.

(51) Int. Cl.
*A61F 9/00* (2006.01)
*A61F 9/007* (2006.01)

(52) U.S. Cl.
CPC .................................. *A61F 9/00763* (2013.01)

(58) Field of Classification Search
CPC ............ A61F 9/00736; A61F 9/00763; A61B 17/32002; A61B 2017/320027; A61B 2217/005
USPC .............................. 606/107, 170, 171; 604/22
See application file for complete search history.

(56) References Cited

U.S. PATENT DOCUMENTS

| | | | |
|---|---|---|---|
| 3,884,238 A | 5/1975 | O'Malley et al. | |
| 3,994,297 A * | 11/1976 | Kopf | 604/22 |
| 4,493,698 A | 1/1985 | Wang et al. | |
| 4,530,356 A | 7/1985 | Helfgott et al. | |
| 4,577,629 A | 3/1986 | Martinez | |
| 4,674,502 A | 6/1987 | Imonti | |
| 4,696,298 A * | 9/1987 | Higgins et al. | 606/171 |
| 4,757,814 A | 7/1988 | Wang et al. | |
| 4,819,635 A | 4/1989 | Shapiro | |
| 4,841,984 A | 6/1989 | Armeniades et al. | |
| 4,909,249 A | 3/1990 | Akkas et al. | |
| 4,940,468 A * | 7/1990 | Petillo | 606/170 |
| 4,986,827 A | 1/1991 | Akkas et al. | |
| 5,019,035 A | 5/1991 | Missirlian et al. | |
| 5,020,535 A * | 6/1991 | Parker et al. | 606/174 |
| 5,024,652 A | 6/1991 | Dumenek et al. | |
| 5,047,008 A | 9/1991 | de Juan, Jr. et al. | |
| 5,059,204 A | 10/1991 | Lawson et al. | |

(Continued)

FOREIGN PATENT DOCUMENTS

EP    0442851 A    8/1991

OTHER PUBLICATIONS

Alcon Research, Ltd., Prior Art Statement, U.S. Appl. No. 12/304,792, Dec. 11, 2014.

*Primary Examiner* — Thomas McEvoy
*Assistant Examiner* — Julie A Szpira (57) ABSTRACT

A vitrectomy probe includes a housing, a fluidic motor disposed within the housing, a needle extending from the housing, and a cutter assembly. The cutter assembly includes an inner cutting member disposed within and axially moveable relative to the needle, a drive shaft disposed within the housing and axially moveable relative to the housing, and a coupler disposed within the housing coupling the drive shaft and the inner cutting member. The motor is associated with the drive shaft in a manner that drives the cutter assembly in an oscillating manner. The probe also includes two or fewer seals within the housing in contact with the cutter assembly for sealing against fluid leakage.

17 Claims, 7 Drawing Sheets

(56) References Cited

U.S. PATENT DOCUMENTS

| | | | | |
|---|---|---|---|---|
| 5,061,238 | A | 10/1991 | Shuler | |
| 5,084,052 | A | 1/1992 | Jacobs | |
| 5,176,628 | A | 1/1993 | Charles et al. | |
| 5,284,472 | A * | 2/1994 | Sussman et al. | 604/22 |
| 5,354,268 | A | 10/1994 | Peterson et al. | |
| 5,380,280 | A | 1/1995 | Peterson | |
| 5,423,844 | A | 6/1995 | Miller | |
| 5,456,689 | A * | 10/1995 | Kresch et al. | 606/180 |
| 5,474,532 | A | 12/1995 | Steppe | |
| 5,520,652 | A | 5/1996 | Peterson | |
| 5,630,827 | A | 5/1997 | Vijfvinkel | |
| 5,674,194 | A | 10/1997 | Jung et al. | |
| 5,733,297 | A | 3/1998 | Wang | |
| 5,782,849 | A | 7/1998 | Miller | |
| 5,810,809 | A * | 9/1998 | Rydell | 606/49 |
| 5,833,643 | A * | 11/1998 | Ross et al. | 604/22 |
| 5,976,121 | A | 11/1999 | Matern et al. | |
| 6,010,496 | A | 1/2000 | Appelbaum et al. | |
| 6,485,499 | B1 * | 11/2002 | Oberkamp et al. | 606/171 |
| 6,488,695 | B1 | 12/2002 | Hickingbotham | |
| 6,514,268 | B2 | 2/2003 | Finlay et al. | |
| 6,575,990 | B1 | 6/2003 | Wang et al. | |
| 6,758,824 | B1 | 7/2004 | Miller et al. | |
| 6,773,445 | B2 | 8/2004 | Finlay et al. | |
| 7,458,940 | B2 * | 12/2008 | Miller | 600/568 |
| 7,549,972 | B2 | 6/2009 | Luloh et al. | |
| 8,216,246 | B2 * | 7/2012 | Luloh et al. | 606/107 |
| 2002/0161398 | A1 | 10/2002 | Hickingbotham | |
| 2003/0078609 | A1 | 4/2003 | Finlay et al. | |
| 2005/0113715 | A1 * | 5/2005 | Schwindt et al. | 600/566 |
| 2005/0156387 | A1 | 7/2005 | Chen et al. | |
| 2006/0271082 | A1 | 11/2006 | Kirchhevel et al. | |
| 2007/0129732 | A1 | 6/2007 | Zacharias | |
| 2007/0185514 | A1 | 8/2007 | Kirchhevel | |
| 2008/0172077 | A1 | 7/2008 | Valencia et al. | |
| 2008/0188881 | A1 | 8/2008 | Chon | |
| 2008/0208233 | A1 | 8/2008 | Barnes et al. | |
| 2009/0163897 | A1 | 6/2009 | Skinner | |
| 2009/0234274 | A1 * | 9/2009 | Luloh et al. | 604/22 |
| 2012/0283741 | A1 | 11/2012 | Luloh et al. | |

* cited by examiner

REDUCED FRICTION VITRECTOMY PROBE

PRIORITY CLAIM

This application claims the benefit of priority of U.S. Provisional Patent Application Ser. No. 61/423,151 titled "Reduced Friction Vitrectomy Probe", filed on Dec. 15, 2010, whose inventor is Brian William McDonell, which is hereby incorporated by reference in its entirety as though fully and completely set forth herein.

BACKGROUND OF THE INVENTION

The present invention relates to vitrectomy probes and more particularly, to vitrectomy probes structurally arranged to operate with a reduced level of friction.

Microsurgical procedures frequently require precision cutting and/or removing various body tissues. For example, certain ophthalmic surgical procedures require cutting and removing portions of the vitreous humor, a transparent jelly-like material that fills the posterior segment of the eye. The vitreous humor, or vitreous, is composed of numerous microscopic fibrils that are often attached to the retina. Therefore, cutting and removing the vitreous must be done with great care to avoid traction on the retina, the separation of the retina from the choroid, a retinal tear, or, in the worst case, cutting and removal of the retina itself In particular, delicate operations such as mobile tissue management (e.g. cutting and removal of vitreous near a detached portion of the retina or a retinal tear), vitreous base dissection, and cutting and removal of membranes are particularly difficult.

The use of microsurgical cutting probes in posterior segment ophthalmic surgery is well known. These cutting probes typically include a hollow outer cutting member, a hollow inner cutting member arranged coaxially with and movably disposed within the hollow outer cutting member, and a port extending radially through the outer cutting member near the distal end thereof Vitreous humor and/or membranes are aspirated into the open port, and the inner member is actuated, closing the port. As the port closes, cutting surfaces on both the inner and outer cutting members cooperate to cut the vitreous and/or membranes, and the cut tissue is then aspirated away through the inner cutting member.

Since vitrectomy probes operate by axial oscillation of one cutting member relative to the other, friction generated by or applied against the oscillating components can affect the efficiency and the performance of the vitrectomy probe. For example, friction may affect or even limit the achievable cut rates with a particular vitrectomy probe. Friction results from a number of factors, including contact points between moving and fixed components within the probe. One example of this includes, for example, movement of the inner cutting member and its driving components relative to fluid and pressure seals within the probe.

One known pneumatic probe system that operates in a suitable manner incorporates four o-ring type seals disposed around an axially oscillating inner cutting member and its driving components, introducing some level of restraining friction. In this known system, the driving components include an aspiration motor tube connected to the inner cutting member. The aspiration motor tube extends through and is driven by a pneumatic diaphragm. Because the aspiration tube extends through the diaphragm, four seals are used to seal the different fluid pressure areas of the probe.

Despite the above described probe system, a need still exists for improved vitrectomy probes. In particular, a need exists for vitrectomy probes that are structurally arranged to have increasingly relatively low friction between components that affect the axial displacement of the cutter.

The present disclosure is directed to addressing one or more of the deficiencies in the prior art.

SUMMARY OF THE INVENTION

In one exemplary aspect, the present disclosure is directed to a vitrectomy probe. The probe includes a housing, a fluidic motor disposed within the housing, a needle extending from the housing, and a cutter assembly. The cutter assembly includes an inner cutting member disposed within and axially moveable relative to the needle, a drive shaft disposed within the housing and axially moveable relative to the housing, and a coupler disposed within the housing coupling the drive shaft and the inner cutting member. The motor is associated with the drive shaft in a manner that drives the cutter assembly in an oscillating manner. The probe also includes two or fewer seals within the housing in contact with the cutter assembly for sealing against fluid leakage.

In some aspects, the inner cutting member comprises a hollow tube forming an aspiration path and having a longitudinal axis. The coupler comprises an aspiration path ending at an aspiration port that is not coaxial with the longitudinal axis.

In another exemplary aspect, the present disclosure is directed to a vitrectomy probe including a housing, a fluidic motor disposed within the housing, a needle extending from the housing, and a cutter assembly. The cutter assembly includes an inner cutting member disposed within and axially moveable relative to the needle, a drive shaft disposed within the housing and axially moveable relative to the housing, and a coupler disposed within the housing coupling the drive shaft and the inner cutting member. The motor is associated with the drive shaft in a manner that drives the cutter assembly in an oscillating manner. The probe also includes a total of two seals within the housing in contact with the cutter assembly for sealing against fluid leakage. The two seals include a first seal and a second seal each sealing about the cutter assembly. The first seal is disposed in fluid communication with at least one air port and prevents fluid flow along the cutter assembly. The second seal is disposed in fluid communication with the aspiration pressure to prevent air flow past the second seal and into aspiration fluid flow.

In another exemplary aspect the present disclosure is directed to a method of manufacturing a vitrectomy probe. The method includes disposing a motor within a housing, disposing a needle to extend from the housing. It also includes assembling a cutter assembly. Assembling the cutter assembly includes the steps of inserting an inner cutting member within the needle in a manner that the inner cutting member is movable relative to the needle, placing a drive shaft within the housing in a manner that the drive shaft is axially moveable relative to the housing, and coupling the drive shaft and the inner cutting member with a coupler. The motor and the drive shaft are associated in a manner that the motor drives the cutter assembly in an oscillating manner. Two or fewer seals are provided within the housing in contact with the cutter assembly for sealing against fluid leakage. This includes steps of sealing about the cutter assembly with a first seal, the first seal being disposed in fluid communication with at least one air port and prevents fluid flow along the cutter assembly, and sealing about the cutter assembly with a second seal, the second seal being disposed in fluid communication with the aspiration pressure to prevent air flow past the second seal and into aspiration fluid flow.

It is to be understood that both the foregoing general description and the following detailed description are exemplary and explanatory only and are intended to provide further explanation of the invention as claimed. The following description, as well as the practice of the invention, sets forth and suggests additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments, examples of which are illustrated in the accompanying drawings. Wherever possible, the same reference numbers are used throughout the drawings to refer to the same or like parts.

The vitrectomy probes and methods described herein are designed to have relatively increased performance levels by including structural arrangements and designs that reduce the overall area of contact of oscillating cutting members, thereby decreasing friction levels when compared to the known probes.

Figure 1:
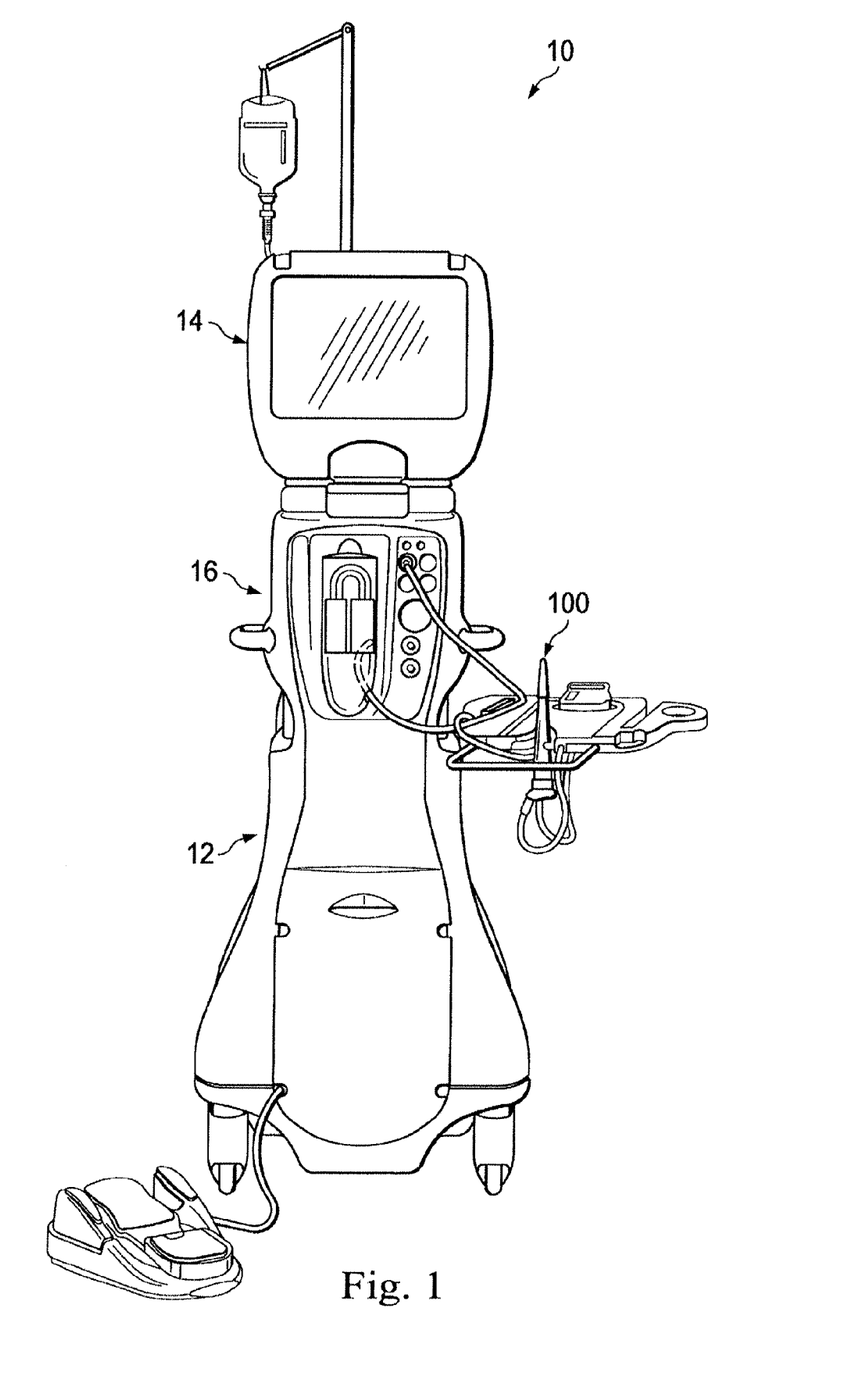
FIG. 1 is an illustration of an exemplary embodiment of a vitrectomy surgical machine.

FIG. 1 illustrates a vitrectomy surgical machine, generally designated 10, according to an exemplary embodiment. The machine 10 includes a base housing 12 and an associated display screen 14 showing data relating to system operation and performance during a vitrectomy surgical procedure. The machine 10 includes a vitrectomy cutter system 16 that includes, among other elements, a vitrectomy cutter 100, a power driving unit, such as a compressor or an external air source for driving the fluidic vitrectomy probe, an aspiration system including a vacuum, and a control unit for operating the components of the system 16.

Figure 2:
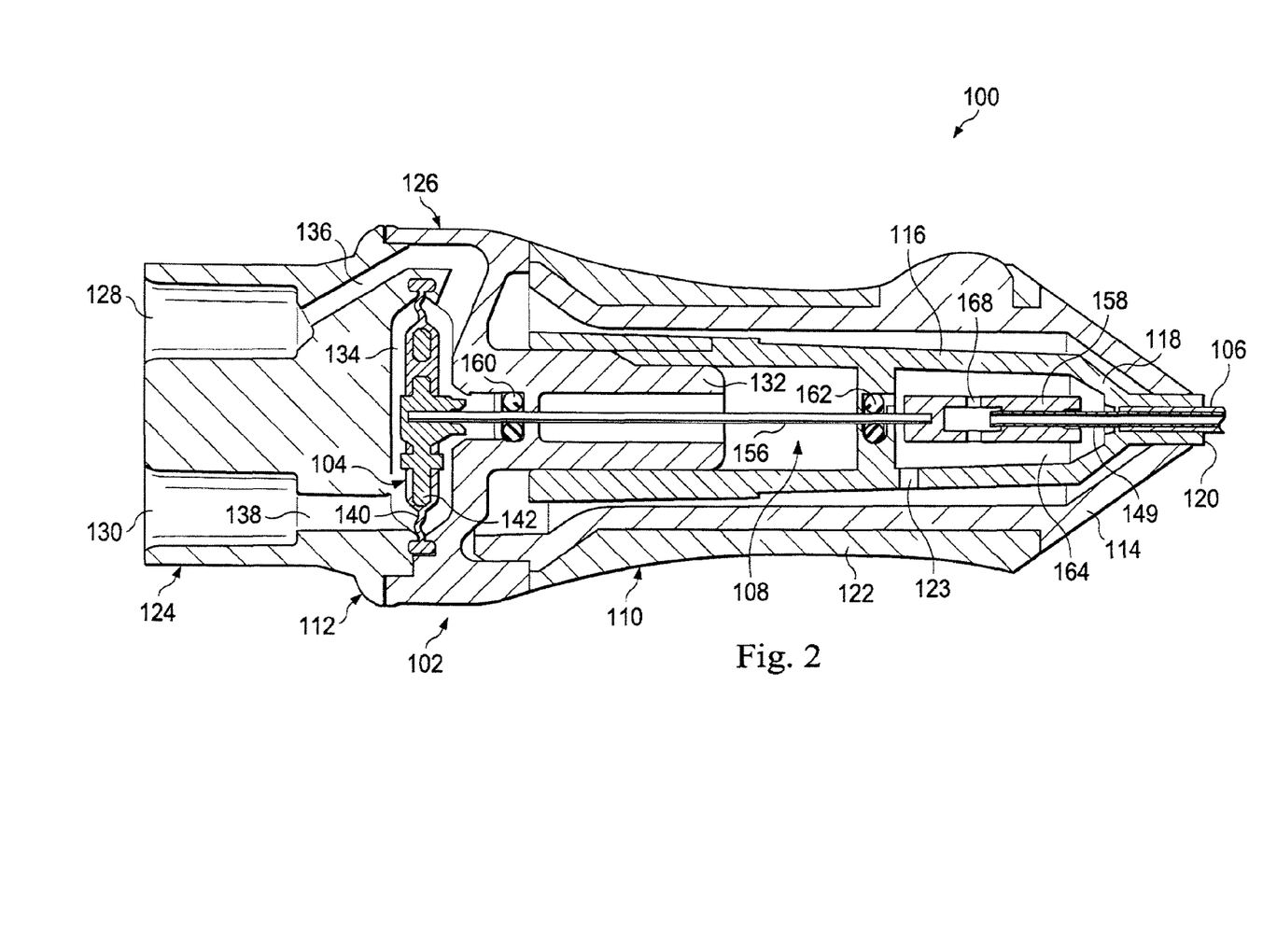
FIG. 2 is an illustration of a cross-sectional view of a vitrectomy probe usable in the vitrectomy surgical machine of FIG. 1 in accordance with the teachings and principles of this disclosure.
Figure 3:
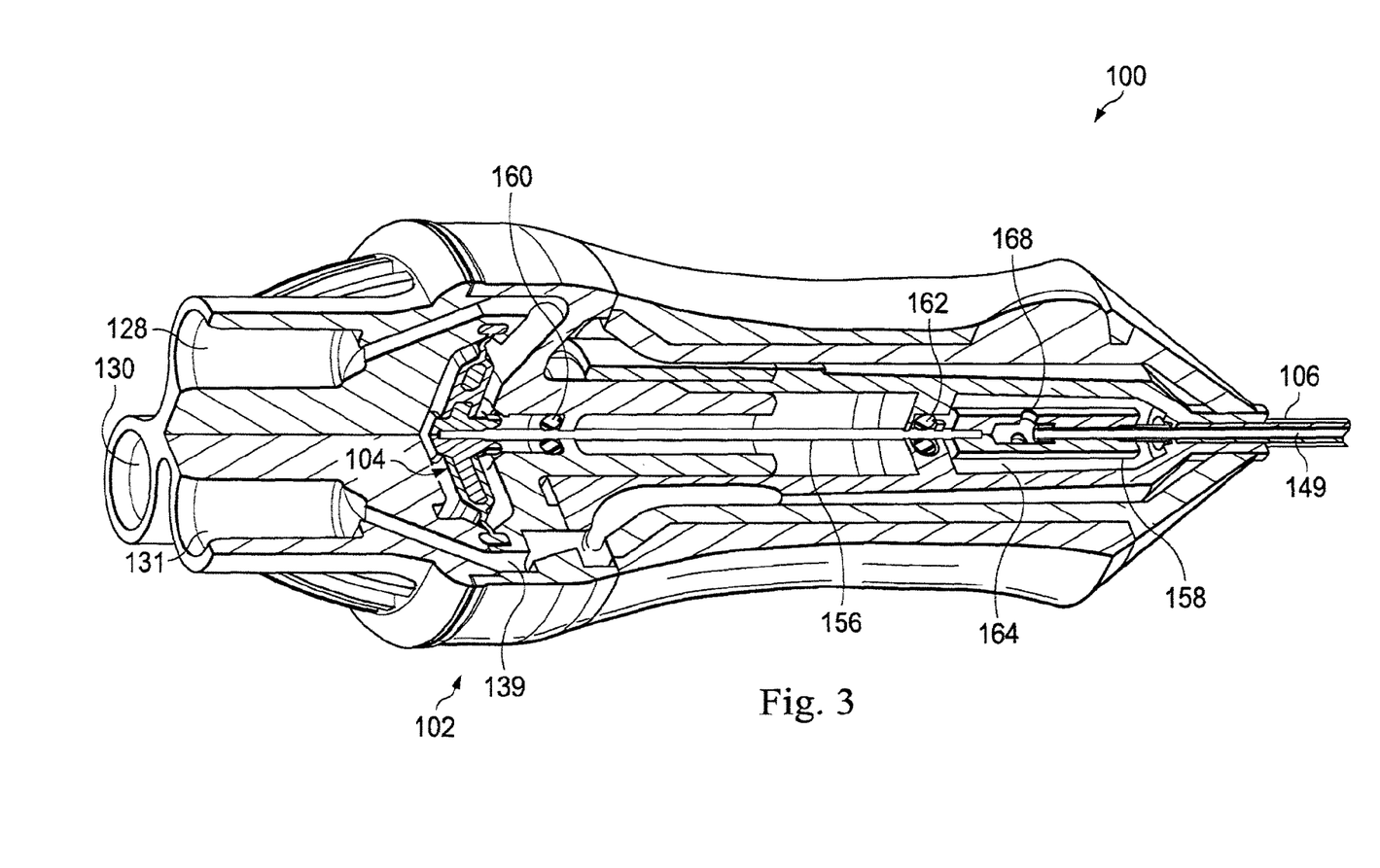
FIG. 3 is an illustration of another cross-sectional view of the vitrectomy probe of FIG. 2 in accordance with the teachings and principles of this disclosure.

FIGS. 2 and 3 show different cross-sectional views of the exemplary vitrectomy probe 100 according to the principles disclosed herein. The probe 100 is used to remove and aspirate tissue, and finds particular utility for removing intraocular tissue during an ophthalmic procedure to re-attach a retina of an eye. Although use in an ophthalmic procedure is described, it is to be understood that the probe 100 can be used to cut and aspirate other tissue, such as removing polyps, fibroids, and other human tissue.

The probe 100 includes a housing 102, a motor 104 disposed within the housing 102, a needle 106 extending from the housing 102, and a cutter assembly 108.

The housing 102 includes a handle portion 110 and a motor portion 112. The handle portion 110 includes a handle body 114, an inner frame 116, and a distal alignment portion 118. The handle body 114 extends in a proximal direction from a distal end 120 toward the motor portion 112. An over-molded grip 122 extends about the handle body 114. The grip 122 may be contoured for comfortable grasping by a user. The inner frame 116 and the alignment portion 118 are, in this embodiment, disposed within the handle body 114. The alignment portion 118 is disposed at the distal end of the handle body 114 and the inner frame 116 connects to the alignment portion 118 and extends rearwardly, in the proximal direction. The inner frame 116 includes an aspiration port 123 that is arranged to permit passage of aspiration fluid, as will be discussed further below.

The motor portion 112 is disposed proximal of the handle portion 110, and includes a rear engine housing 124 and a front engine housing 126. The rear engine housing 124 includes communication ports 128, 130 that provide communication between the vitrectomy probe 100 and the surgical machine 10. It also includes an aspiration port 131 (FIG. 3) that provides communication between an aspiration pump at the surgical machine 10 and the probe 100. In this embodiment, the communication ports 128, 130 are air ports, and the motor portion 112 is configured to hold a fluidically driven motor, such as, for example, a pneumatically driven motor.

The ports 128, 130, 131 extend from the proximal end of the rear engine housing 124 toward the distal end of the rear engine housing 124. The front engine housing 126 is disposed distal of the rear engine housing 124 and is arranged to interface with the handle portion 110. As will become more apparent below, the rear engine housing 124 is configured to provide communication to the surgical machine 10, and the front engine housing 126 cooperates with the rear engine housing 124 to securely support the motor 104 of the vitrectomy probe 100.

In the embodiment shown, the front engine housing 126 includes a central protrusion 132 that extends in the distal direction to engage the inner frame 116. In this embodiment, the rear engine housing 124 and the front engine housing 126 are shaped to cooperatively form a motor chamber 134. In this embodiment, the chamber 134 is a transversely extending hollow configured to hold the motor 104 for driving the cutter assembly 108. The rear engine housing 124 and front engine housing 126 include passages 136, 138 that respectively extend between the rear engine housing communication ports 128, 130 and the motor chamber 134. In the embodiment of FIG. 2, the ports 128, 130 are in fluid communication with opposing sides of the motor chamber 134, and here, are in communication with distal and the proximal portions of the motor chamber 134. Likewise, the ports 128, 130 are in fluid communication with opposing sides of the motor 104. The rear engine housing 124 and front engine housing 126 also include a passage 139 extending from the aspiration port 131 to the handle body 114, as seen in FIG. 3. The passage 139 is in fluid communication, through a passage in the handle body 114 or the inner frame 116, with the aspiration port 123 in the inner frame 116 and accommodates the flow of aspiration fluid from the handpiece 100.

The motor 104 is disposed within the motor chamber 134 and is configured to drive the cutter assembly 108. In this way, the cutter assembly 108 can be used to cut and aspirate tissue, such as intraocular or other tissue. The motor 104, in this embodiment is a pneumatically driven motor, formed of a flexible diaphragm 140 and a rigid coupler 142. It operates by pressure variation between the first and second ports 128, 130 and thus, on opposing sides of the motor 104. The variation in pressure on opposing sides of the motor 104 within the motor chamber 134 causes the diaphragm 140 to vibrate, carrying the rigid coupler 142 in a back-and-forth oscillating motion.

The distal end of the pneumatic probe 100 includes the needle 106. The needle 106 is a hollow cylinder and extends from the housing 102 and is supported by the alignment portion 118. It includes a closed end and an outer port that receives tissue, such as ophthalmic tissue, and it cooperates with the cutter assembly 108 to cut tissue.

Figure 4:
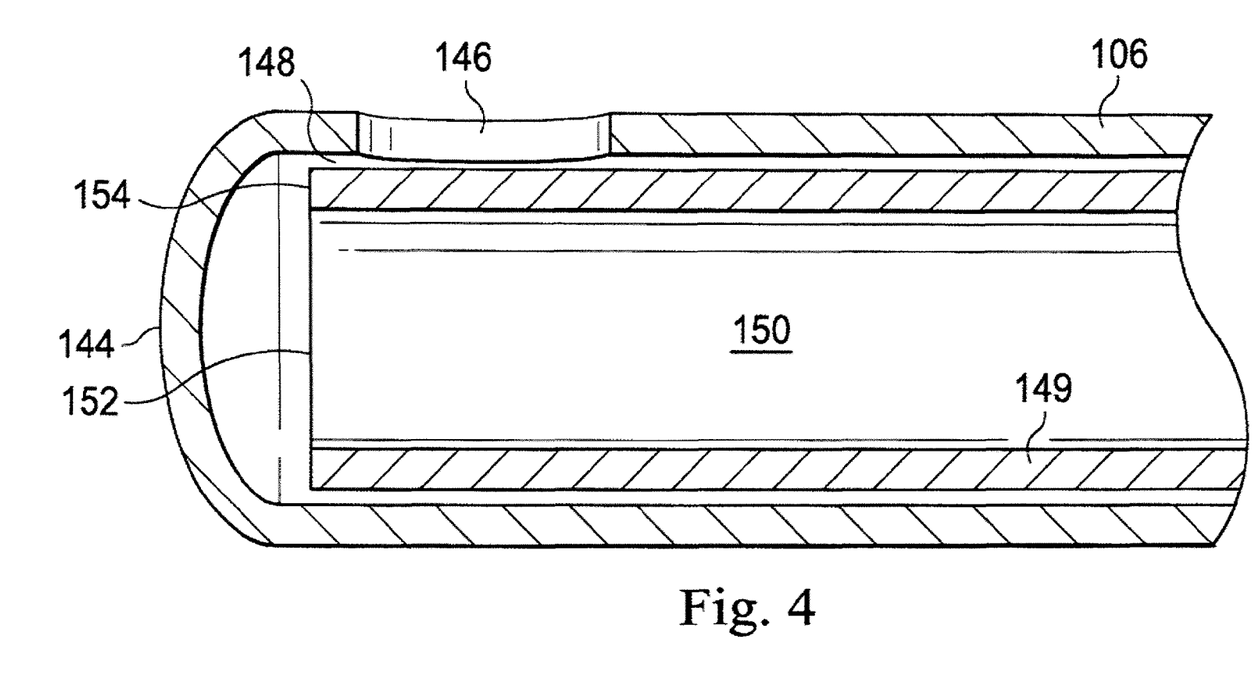
FIG. 4 is an illustration of a cross-sectional view of a distal end of a cutting needle of the vitrectomy probe of FIG. 2 in accordance with the teachings and principles of this disclosure.

A distal end of the needle 106 is shown in FIG. 4. The needle 106 includes a closed end 144 and an outer port 146 that receives tissue, such as ophthalmic tissue. The outer port 146 is in fluid communication with an inner channel 148. An inner cutting member 149 is located within the inner channel 148 of the needle 106. The inner cutting member 149 has an inner bore 150, an open end 152, and a cutting surface 154. As will be described below, the inner bore 150 is in fluid communication with the aspiration line of the vitrectomy probe 100. The aspiration line connects to a vacuum pressure that pulls tissue into the outer port 146 when the inner cutting member 149 is located away from the port 146. The inner cutting member 149 moves within the inner channel 148 of the needle 106 to cut tissue that is pulled into the outer port 146 by the aspiration system. The ophthalmic tissue received by the outer port 146 is preferably vitreous or membranes.

Returning to FIGS. 2 and 3, the cutter assembly 108 includes a drive shaft 156, a coupler 158, and the inner cutting member 149. As shown in FIG. 2, the drive shaft 156 connects to and extends from the motor 104 and extends substantially centrally through the central protrusion 132 of the motor portion 112. The drive shaft 156 is a solid rod structurally configured to transmit loading applied by the motor 104 to the other components of the cutter assembly 108. The coupler 158 couples the distal end of the drive shaft 156 to the proximal end of the inner cutting member 149. In this embodiment, the drive shaft 156, the coupler 158, and the inner cutting member 149 are all coaxially aligned in the vitrectomy probe 100.

To accommodate aspiration fluid and tissue flowing through the inner cutting member 149, the coupler 158 is hollow, having a chamber therein. It comprises an aspiration port 168 extending from the hollow or chamber of the coupler 158 to an aspiration chamber 164, formed by the inner frame 116 that surrounds the coupler 158. In the embodiment shown the aspiration port 168 is formed to be not coaxial with a central axis of the inner cutting member or the cutter assembly.

The aspiration port 123 through the inner frame 116 connects the aspiration chamber 164 to an aspiration line through a passage in the handle body 114 or the inner frame 116, to the passage 139, as best seen in FIG. 3.

As the drive shaft 156 axially translates in a distal and proximal direction, the coupler 158, fixed to the drive shaft 156, also translates in an oscillating manner within the aspiration chamber 164. Because the inner cutting member 149 is fixed to the coupler 158, axial displacement or translation of the coupler 158 results in axial displacement or translation of the inner cutting member 149 relative to the needle 106. Through the coupler 158, the interior of the inner cutting member 149 is in fluid communication with the aspiration chamber 164.

In this embodiment, the vitrectomy probe 100 comprises two seals cooperating with the cutter assembly 108. In this embodiment, the seals are o-ring seals, although other seals may be used. A first seal 160 is disposed within the central protrusion 132 of the motor portion 112. In this embodiment, the seal 160 extends about the drive shaft 156. It is configured and arranged to seal the motor chamber 134 from probe components disposed distally of the first seal 160. As can be seen, the front seal 160 is in fluid communication with the air port 128 and prevents fluid flow from leaving the motor chamber and flowing along the cutter assembly. In this embodiment, a second seal 162 is disposed in the inner frame 116. In this embodiment the second seal 162, like the first seal 160, also extends about the drive shaft 156. Here the second seal 162 seals the aspiration chamber 164 from other components or regions of the vitrectomy probe 100. In this case, the second seal 162 is disposed in fluid communication with the vacuumed aspiration fluid and prevents external fluid or other air flow from entering the aspiration fluid.

Known vitrectomy probes aspirate through a central aspiration tube extending from the needle through the motor to an aspiration port at the proximal end of the probe. The motor drives the central aspiration tube, which drives the cutter in the needle. Three seals are used to isolate the opposing sides of the motor chamber. A least one additional seal is located distally, along the cutter, isolating the needle. During use, the axial vibration of the motor must overcome the frictional resistance of the at least four seals on the central aspiration tube and on the cutter.

The exemplary vitrectomy probe 100 shown in FIGS. 2 and 3 however, includes a coupler 158 and aspiration chamber 164 disposed distally of the motor 104. Accordingly, the motor shaft 156 does not carry aspiration fluid, and therefore, it does not need to extend through the motor 104, but instead it extends to and ends at the motor 104. As such, rather than having four seals that result in frictional resistance to oscillating motion or vibration, the embodiment in FIGS. 2 and 3 includes only two seals in contact with the cutter assembly 108. This results in lower frictional resistance on the cutter assembly 108, increasing the efficiency of the probe operation and allowing cutting rates that may not be feasible with the known system.

The arrangement shown also results in additional efficiencies. The known device uses a central aspiration tube sized to convey or carry aspirating fluid. Accordingly the aspiration tube has a relatively large diameter. The seals slide along the diameter, and are in contact with the tube over a relatively large area. In contrast, the embodiment in FIGS. 2 and 3 employs the drive shaft 156, which is a relatively small diameter solid shaft used to drive the inner cutting member 149. Because it need not convey aspiration fluid, it can have a smaller diameter. In some examples, the drive shaft 156 has a diameter approximately in the range of about 0.020-0.030 inch. This is much smaller than a conventional drive shaft of about 0.050 inch. This smaller diameter further decreases the area of contact with the seals, resulting in lower frictional resistance during oscillating vibration. By reducing the number of seals in the vitrectomy probe and by reducing the contact area for each seal in the vitrectomy probe, the vitrectomy probe 100 disclosed herein can operate more efficiently and with lower variations in pressure to achieve the same operating parameters as conventional probes.

Figure 5:
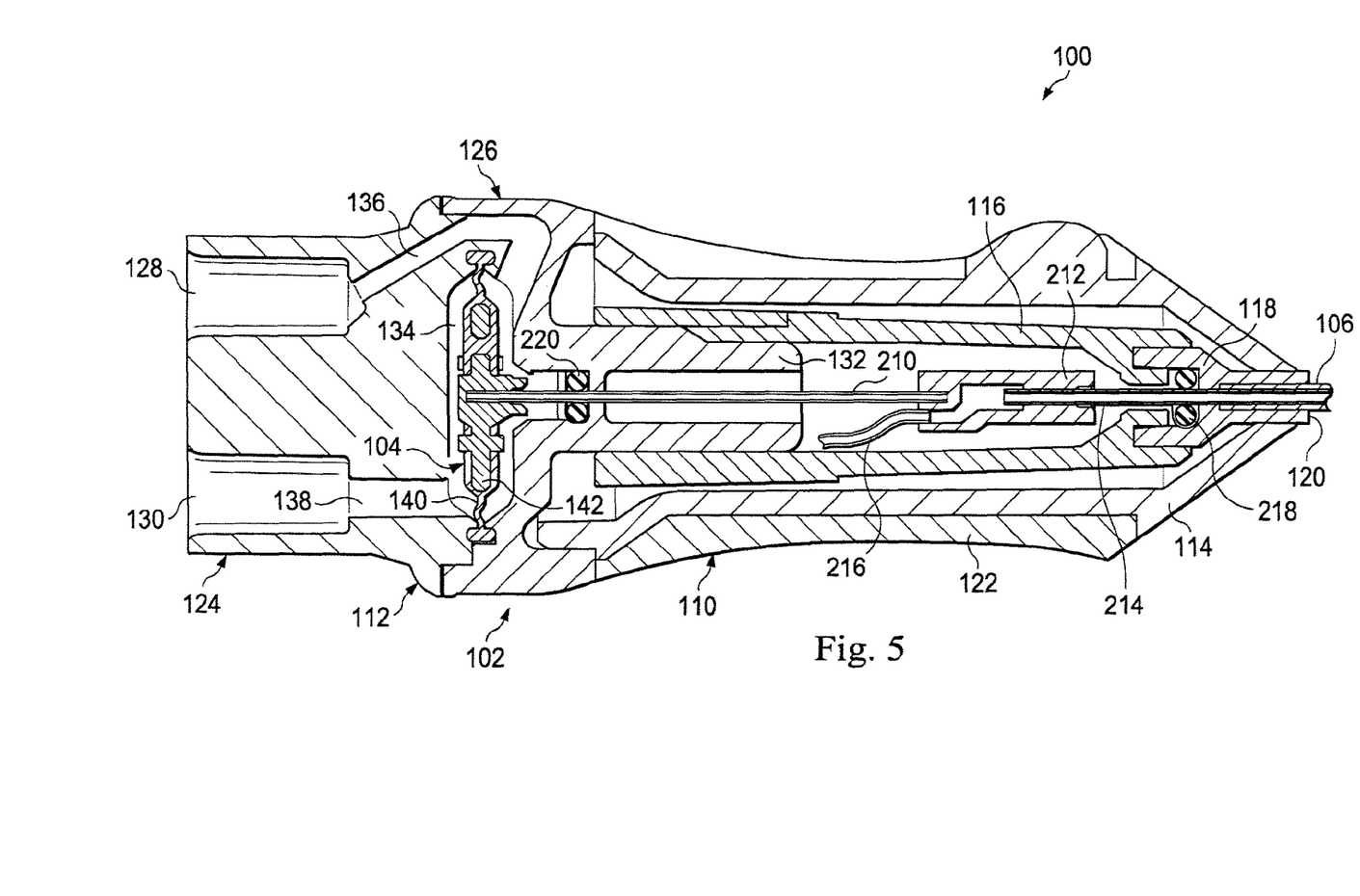
FIG. 5 is an illustration of a cross-sectional view of another embodiment of a vitrectomy probe usable in the vitrectomy surgical machine of FIG. 1 in accordance with the teachings and principles of this disclosure.
Figure 6:
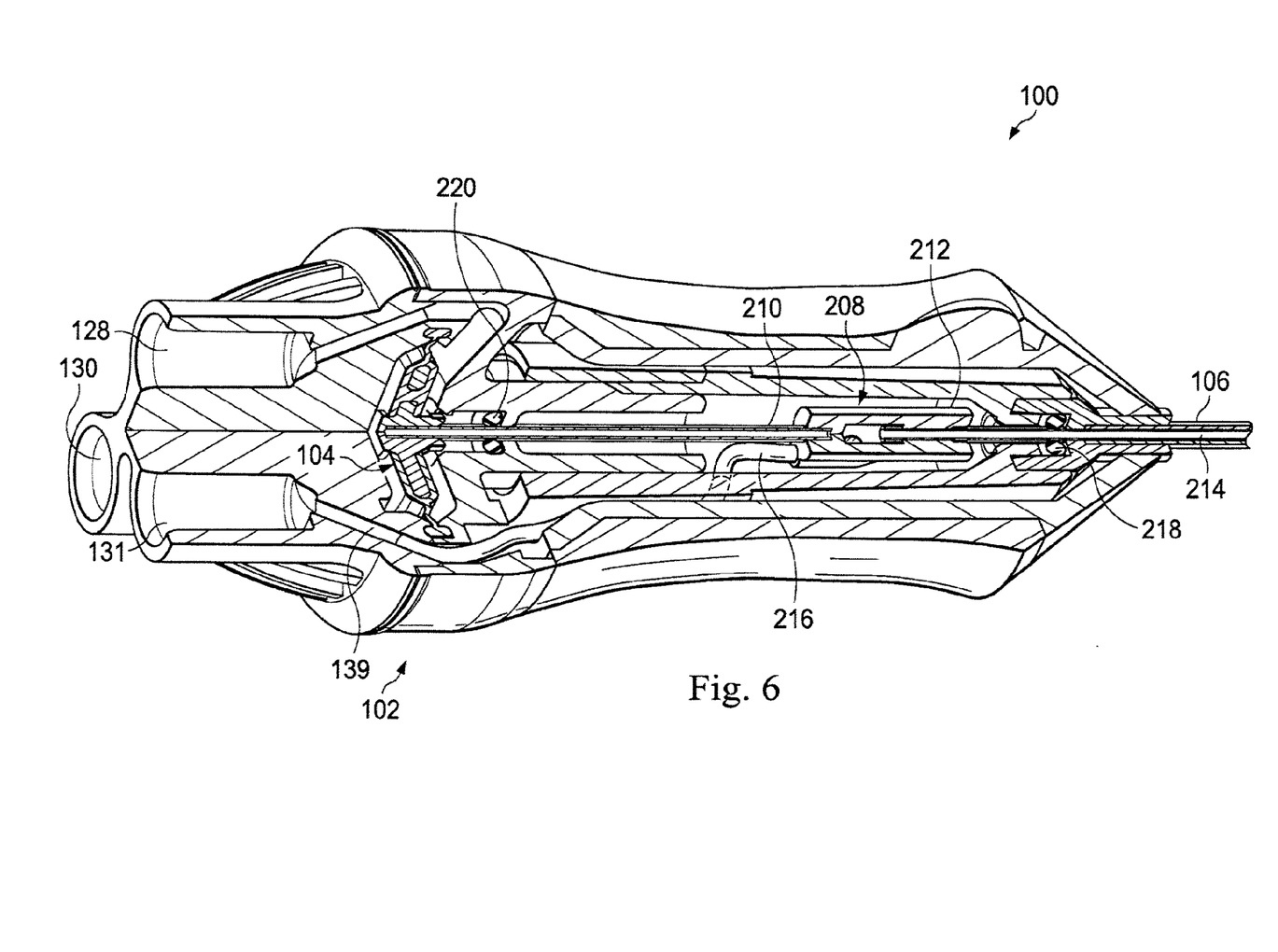
FIG. 6 is an illustration of another cross-sectional view of the vitrectomy probe of FIG. 5 in accordance with the teachings and principles of this disclosure.

FIGS. 5 and 6 show another embodiment of a vitrectomy probe 100 in accordance with the principles of the present disclosure. There are many similarities between the embodiment in FIGS. 5 and 6 and the embodiment described above. For the sake of efficiency, the below discussion is primarily focused on the differences between the embodiments. It should be apparent that much of the description above applies to the embodiment in FIGS. 5 and 6.

Like the probe discussed above, the probe 100 in FIGS. 5 and 6 includes a housing 102, a motor 104 disposed within the housing 102, and a needle 106 extending from the housing 102. It also includes a cutter assembly 208 with some features that vary from the embodiment described above.

In this assembly, the cutter assembly 208 includes a drive shaft 210, a coupler 212, and an inner cutting member 214. The drive shaft 210 connects to and extends from the motor 104. In this embodiment, as an example only, the drive shaft 210 is a tubular rod structurally configured to transmit loading applied by the motor 104 to the other components of the cutter assembly 108. However, the tubular drive shaft 210 is not used to convey aspiration fluid and therefore, it ends at the motor 104. In other embodiments, the drive shaft 210 may be a solid shaft so that it has a smaller diameter to achieve the frictional advantages discussed above. The coupler 212 couples the distal end of the drive shaft 210 to the proximal end of the inner cutting member 214.

To accommodate aspiration fluid and tissue flowing through the inner cutting member 214, the coupler 212 is a hollow coupler that also couples a flexible aspiration tube 216 to the inner cutting member 214. Accordingly, similar to the coupler 158 described above, the coupler 212 includes a passage or chamber and an aspiration port arranged for the passage of the aspiration fluid. As can be seen, the aspiration port is not coaxial with an axis though the cutter assembly 208. Instead, in this embodiment, the port is arranged parallel to, but offset from an axis through the cutter assembly 208. The flexible tube 216 is connected to the aspiration port on the coupler 114. The flexible tube 216 is arranged to fluidly connect to the aspiration passage 139, as shown in FIG. 6. When the motor is driving the cutter assembly 208, the flexible aspiration tube flexes to accommodating axial displacement of the coupler due to the oscillating motion of the coupler.

Like the embodiment described above, the vitrectomy probe 100 in FIGS. 5 and 6 comprises only two seals cooperating with the cutter assembly 208. A first seal 218 is disposed within the central protrusion 132 of the motor portion 112, about the drive shaft 210. A second seal 220 is disposed in the alignment portion 118. In this embodiment, the second seal 220 extends about the inner cutting member 214.

The exemplary probes disclosed herein may be manufactured for distribution with a surgical machine 10 or independent of the surgical machine 10. Some embodiments of the probe are assembled by providing the various components of the oscillating probe described above. The components are then assembled by disposing the pneumatic motor 104 within the housing 102. Since the pneumatic motor 104 extends between the rear engine housing 124 and the front engine housing 126, care may be taken to insert edges of the motor 104, which may be formed as a part of the flexible diaphragm 140, into accommodating portions in the rear engine housing 124 and the front engine housing 126. The needle 106 is then disposed to extend from the housing 102. The cutter assembly is introduced to the housing 102. It is assembled by inserting the inner cutting member 149 within the needle 106 in a manner that the inner cutting member 149 is movable relative to the needle 106. The drive shaft 156 is introduced into the housing in a manner that the drive shaft is axially moveable relative to the housing. It is secured to the motor 104 in a manner that the motor can axially displace the drive shaft 156 in an oscillating manner. The drive shaft 156 is coupled to the coupler 158, and the coupler 158 is coupled to the inner member 149.

The manufacturer may introduce two or fewer seals within the housing in contact with the cutter assembly for sealing against fluid leakage. The first seal 160 is introduced into the front engine housing 126 and is disposed about the motor shaft 156. This includes placing the seal so that it seals the motor chamber 134 and prevents pneumatic fluid from the air port 128 from flowing along the cutter assembly 108. The second seal 162 is introduced to the housing 102 around the cutter assembly 108 to seal from liquid aspiration fluid. It should be apparent that the order manufacturing may differ from that described herein, and unless otherwise indicated, the order of the manufacturing steps recited in the claims may be in any order unless otherwise indicated.

Figure 7:
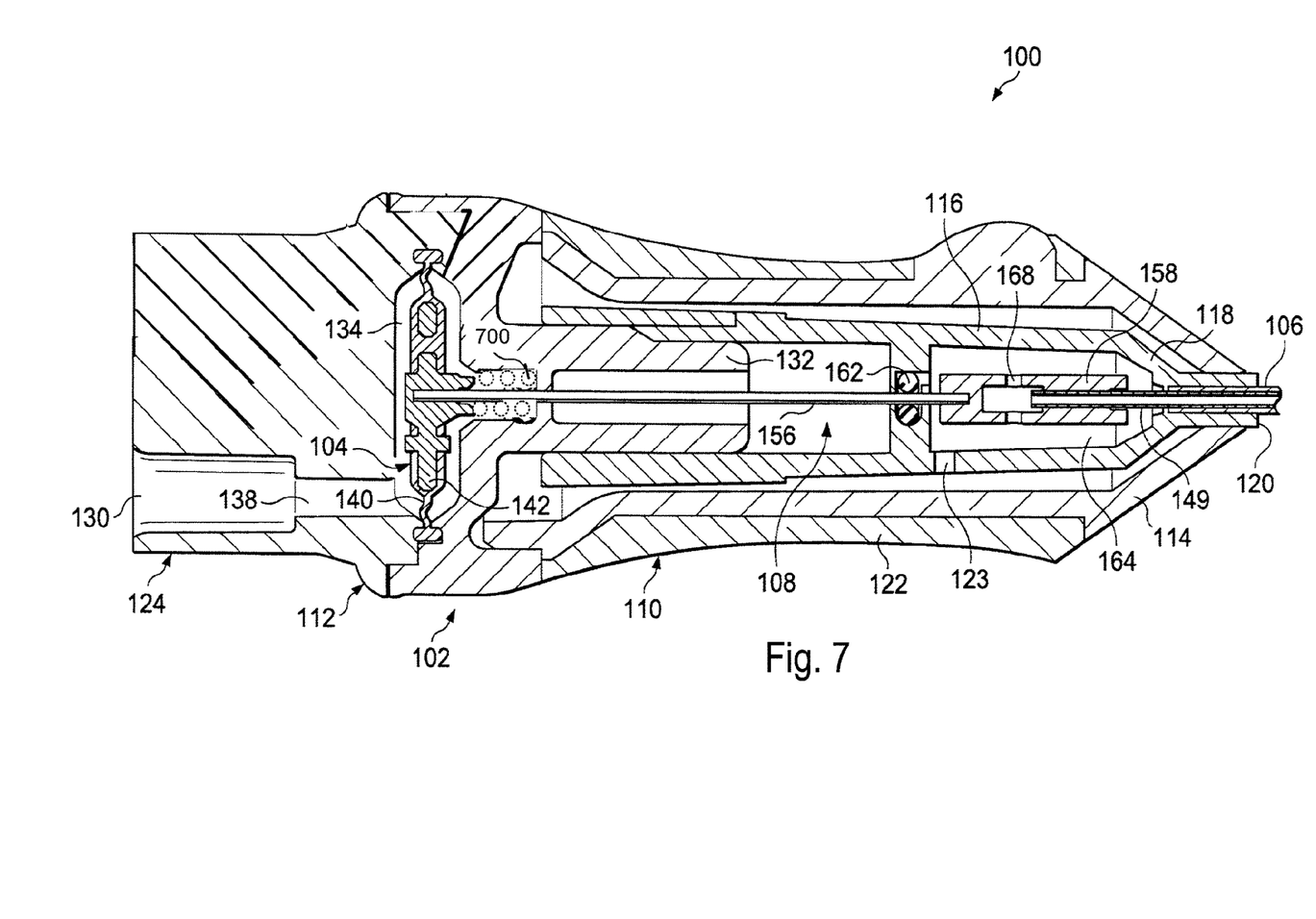
FIG. 7 is an illustration of another embodiment of the vitrectomy probe showing a single air port and a biasing device in accordance with the teachings and principles of this disclosure.

Although the embodiments shown are illustrated with two air ports in communication with opposing sides of the diaphragm, additional embodiments include a single air port 130 (e.g., as seen in FIG. 7) in communication with a proximal side of the diaphragm and a biasing member, such as a spring 700, that acts against the distal side of the diaphragm. In this arrangement, only a single seal 162 is required to seal against fluid leakage.

It should be appreciated that although several different embodiments are shown, any of the features of one embodiment may be used on any of the other embodiments shown. Other embodiments will also be apparent to those skilled in the art from consideration of the specification and practice of the embodiments disclosed herein. It is intended that the specification and examples be considered as exemplary only, with a true scope and spirit of the invention being indicated by the following claims.

I claim:

1. A vitrectomy probe, comprising:
   a housing;
   a fluidic motor disposed within the housing, wherein the motor comprises a diaphragm connected to the drive shaft in a manner that drives the drive shaft in an oscillating manner;
   a needle extending from the housing,
   a cutter assembly comprising:
      an inner cutting member, comprising an aspiration path, disposed within and axially moveable relative to the needle;
      a drive shaft disposed within the housing and axially moveable relative to the housing; and
      a coupler disposed within the housing coupling the drive shaft and the inner cutting member, wherein the inner cutting member, drive shaft and coupler are co-linear such that axial motion of the drive shaft causes axial motion of the inner cutting member, and
      wherein the coupler diverts the aspiration path, from the inner cutting member, away from the drive shaft such that the aspiration path does not flow through the drive shaft;
   the motor being associated with the drive shaft in a manner that drives the cutter assembly in an oscillating manner; and
   two or fewer seals within the housing for sealing against fluid leakage, wherein a first seal of the two or fewer seals is in contact with the inner cutting member and wherein a second seal of the two or fewer seals is in contact with the drive shaft between the motor and the coupler.

2. The vitrectomy probe of claim 1, wherein the inner cutting member comprises a hollow tube forming the aspiration path and having a longitudinal axis, and wherein the coupler comprises an aspiration path ending at an aspiration port that is not coaxial with the longitudinal axis.

3. The vitrectomy probe of claim 2, wherein the aspiration port is transverse to the longitudinal axis of the aspiration path in the inner cutting member.

4. The vitrectomy probe of claim 2, further comprising a flexible aspiration tube associated with the aspiration port on the coupler, the flexible aspiration tube accommodating and flexing as a result of the axial oscillating movement of the coupler.

5. The vitrectomy probe of claim 2, wherein the aspiration port in the coupler exits into a chamber containing the coupler, the vitrectomy probe further comprising an aspiration path extending from the chamber containing the coupler to a proximal end of the housing.

6. The vitrectomy probe of claim 1, wherein the housing comprises
a first air port and a second air port, the first and second air ports being in fluid communication with opposing sides of the diaphragm.

7. The vitrectomy probe of claim 1, wherein the housing comprises a motor chamber having a distal wall and a proximal wall, wherein the proximal wall of the motor chamber is solid and the distal wall of the motor chamber includes a passage for the drive shaft.

8. The vitrectomy probe of claim 1, wherein the second seal is disposed in fluid communication with a motor chamber in a manner that prevents fluid flow along the cutter assembly.

9. The vitrectomy probe of claim 8, wherein the first seal is disposed about the inner cutting member to prevent the aspiration of air past the first seal between the inner cutting member and the needle into the fluid flow.

10. The vitrectomy probe of claim 1, wherein the drive shaft is a solid shaft extending to the coupler, the solid shaft having a minimized diameter to decrease the surface area contact of the seals resulting in decreased friction.

11. The vitrectomy probe of claim 1, wherein at least a portion of the aspiration path exiting the coupler is parallel to, but not collinear with, the drive shaft.

12. The vitrectomy probe of claim 1, wherein the entire drive shaft is collinear with the inner cutting member.

13. A vitrectomy probe, comprising:
a housing,
a fluidic motor disposed within the housing, wherein the motor comprises a diaphragm connected to the drive shaft in a manner that drives the drive shaft in an oscillating manner;
a needle extending from the housing, the needle comprising an outer cutting member,
a cutter assembly comprising:
an inner cutting member, comprising an aspiration path, disposed within and axially moveable relative to the needle;
a drive shaft disposed within the housing and axially moveable relative to the housing;
a coupler disposed within the housing coupling the drive shaft and the inner cutting member, wherein the inner cutting member, drive shaft and coupler are co-linear such that axial motion of the drive shaft causes axial motion of the inner cutting member, and
wherein the coupler diverts the aspiration path, from the inner cutting member, away from the drive shaft such that the aspiration path does not flow through the drive shaft;
the motor being associated with the drive shaft in a manner that drives the cutter assembly in an oscillating manner;
a total of two seals within the housing for sealing against fluid leakage, the total of two seals comprising:
a first seal sealing about the cutter assembly, the first seal being disposed in fluid communication with at least one air port and prevents fluid flow along the cutter assembly; and
a second seal sealing about the cutter assembly, the second seal being disposed in fluid communication with the aspiration pressure to prevent air flow past the second seal and into aspiration fluid flow.

14. The vitrectomy probe of claim 13, wherein the inner cutting member comprises a hollow tube forming the aspiration path and having a longitudinal axis, and wherein the coupler comprises an aspiration path ending at an aspiration port that is not coaxial with the longitudinal axis.

15. The vitrectomy probe of claim 13, wherein the drive shaft is a solid shaft extending to the coupler, the solid shaft having a minimized diameter to decrease the surface area contact of the seals resulting in decreased friction.

16. The vitrectomy probe of claim 13, wherein at least a portion of the aspiration path exiting the coupler is parallel to, but not collinear with, the drive shaft.

17. The vitrectomy probe of claim 13, wherein the entire drive shaft is collinear with the inner cutting member.

* * * * *